United States Patent [19]

Tse

[11] Patent Number: 4,866,991
[45] Date of Patent: Sep. 19, 1989

[54] STRETCHABLE FIBER MEASUREMENT STATION

[76] Inventor: Ming K. Tse, 4 Flint Lock Rd., Lexington, Mass. 02173

[21] Appl. No.: 234,897

[22] Filed: Aug. 22, 1988

[51] Int. Cl.$^4$ .............................................. G01N 3/10
[52] U.S. Cl. ........................................ 73/837; 73/37.5
[58] Field of Search ................. 73/837, 37.5, 37, 807, 73/838, 840

[56] References Cited

U.S. PATENT DOCUMENTS

| | | | |
|---|---|---|---|
| 3,580,050 | 5/1971 | Waldron | 73/37 |
| 3,908,057 | 9/1975 | Smith | 428/151 |
| 3,914,498 | 10/1975 | Videen | 428/290 |
| 3,940,917 | 3/1976 | Strachan | 57/152 |
| 3,967,497 | 7/1976 | Brown | 73/141 |
| 3,981,415 | 9/1976 | Fowler et al. | 222/95 |
| 3,983,870 | 10/1976 | Herbert et al. | 128/165 |
| 3,991,604 | 11/1976 | Hayes et al. | 73/37 |
| 4,052,866 | 10/1977 | Saunders | 66/193 |
| 4,106,313 | 8/1978 | Boe | 66/202 |
| 4,223,632 | 9/1980 | Caldwallader | 118/58 |
| 4,442,474 | 4/1984 | de Jong et al. | 361/283 |
| 4,715,235 | 12/1987 | Fukui et al. | 73/862.68 |

OTHER PUBLICATIONS

"Mechanics of Form-Persuasive Garments Based on Spandex Fibers", Textile Research Journal, Sep. 1988, by Salim M. Ibrahim, pp. 950–963.
"Elastic Properties of Twill and Modified Twill Warp Knitted Elastic Fabrics", Part I: Fabric Production and Testing, by W. D. Cooke and G. S. Assimakopoulos, Textile Research Journal 8/85, pp. 452–460.
"Mechanism for Stretch and Recovery Properties of Certain Stretch Fabrics", by A. S. Cooper, Jr., et al, Textile Research Journal, 5/65, pp. 452–458.
"The Effect of Fabric Structure on the Properties of Two-Way Stretch Fabrics Made from Elastic Core-Spun Yarns of Cotton and Wool Blend", by A. P. Singh Sawhney, Textile Res. Journal, 7/74, pp. 506–512.
"Fundamental Relationship of Fabric Extensibility to Anthropometric Requirements and Garment Performance", by Wm. Kirk, Jr. et al, Textile Research Journal, 1/66, pp. 37–47.
"Simulation of Garment Pressure in Wear by Strip Bi-axial Extension of Cylindrically Sewn Fabrics", by Tsuneo Horino, et al, Journal of Textile Mach. Soc. of Japan, vol. 23, No. 2, (1977), pp. 41–46.
"The Theoretical Behavior of a Knitted Fabric Subjected to Biaxial Stresses", by Peter Popper, Textile Research Journal, 2/66. pp. 148–157.
"Three-Dimensional Analysis of a Plain Knitted Fabric Subjected to Biaxial Stresses", by J. M. Whitney et al., Textile Research Journal, 2/66, pp. 143–147.
"Letters to the Editor", Textile Research Journal, 10/67, pp. 908–911.
"A Device for Measuring Stress-Strain Behavior of Low-Modulus Textiles Under Uniform Radial Strainint", by Charles B. Hassenboehler et al, Textile Research Journal, 3/74, pp. 188–192.
"Physical Properties of Weft Knitted Fabrics", by Witold Zurek et al, Textile Research Journal, 4/86, pp. 241–248.

Primary Examiner—Jerry W. Myracle

[57] ABSTRACT

Apparatus and method for determining and comparing the stretchability of fabrics. The apparatus and method comprise a support tube upon which is mounted one or more annular, inflatable bladders. A stretchable fabric sample is pulled over the support and the deflated bladder and secured in place by a collar. Air is directed from a pressure source through the support tube to inflate the bladder at a fixed rate. Electronic sensors measure the air pressure required to inflate the bladder and expand the fabric as a function of time during inflation and this inflation data is applied to a computer. The computer plots the air pressure required to inflate the bladder as a function of time for both cases, where fabric is and is not in place. The deformation characteristic of one or more fabric samples can thereby be observed.

12 Claims, 4 Drawing Sheets

STRETCHABLE FIBER MEASUREMENT STATION

FIELD OF THE INVENTION

The present invention relates to an apparatus and method for measuring stretch characteristics of fabrics and in particular to a tube mounted inflatable bladder connected to an air supply and electronic means for measuring and comparing stretch against time.

BACKGROUND OF THE INVENTION

Support hose is typically utilized to place some or all of the lower limbs of a wearer under a predetermined containment pressure. One typical example is for use on post-operative patients to prevent swelling. In other instances support hose is commonly utilized on a daily basis to provide support for various medical or aesthetic reasons.

In these and many other applications, fabric is commonly woven today with a stretch characteristic in one or more directions. The stretch of such stretch fabrics is typically achieved through a combination of weaving characteristics and of the filamentary, including elastomeric, yarns or threads utilized in the weaving operation. In most of these applications it is important to control the stretch characteristic to within predetermined limits. To achieve such control requires increased on-line quality assurance testing of the fabric at predetermined times during the manufacturing process in order to determine the consistency of its stretch.

Prior art techniques for measuring stretch have been awkward and clumsy and have not yielded to online monitoring of the production of stretch fabric. In one such example, as shown in U.S. Pat. No. 4,106,313, the material is mechanically pulled to determine stretch. By its nature, this technique is not only awkward but limited in the accuracy of its one-dimensional determination of stretch.

SUMMARY OF THE INVENTION

According to the teaching of the present invention, a system is provided for computer automated online testing of the stretch characteristics of support hose and other stretch weave fabrics.

The apparatus of the present invention comprises a cantilevered tube over which a length of hose or other material in the form of a tube is slipped. Mounted around the tube are one or more inflatable bladders which expand under air pressure in a smooth annular shape. Each bladder is pressurized by air ducted through the support tube and into the inflatable bladder. The stretch hose is secured on the support tube by a restraining collar.

A pressurized air source applies air to each bladder through a respective rate control valve, manifold and the support tube to inflate each bladder. The rate control valve provides an accurate correlation between time and volume of air supplied to each bladder. A sensor measures the pressure of the air in ducts which pressurize each bladder; one sensor and control valve for each bladder. Each pressure sensor, in turn, provides an electronic output representing air pressure within the corresponding bladder to a computer where the pressure data is stored as a function of time, and thus of applied volume. The stored data is plotted with air pressure shown as a function of time.

The system is calibrated by running a bladder pressurization cycle and collecting data first without any fabric around the support tube. The cycle is then repeated with various test fabrics in place on the tube to provide the observer with a comparison of the stretchability of fabric samples against a control sample.

In this fashion hose or other fabric can be taken directly from the production line at production line sites, slipped over the test fixture and then rapidly tested and returned to the production line while the computer assembles data and plots a profile of the pressure response of the fabric at one or more locations along its length. The thus assembled data and plots will give production line monitors the opportunity to quickly determine the consistency of stretch characteristics in the tubular shaped fabric as it is manufactured.

DETAILED DESCRIPTION OF THE DRAWING

The invention will be more fully understood from the following, solely exemplary, detailed description taken in conjunction with the accompanying drawings in which.

DETAILED DESCRIPTION OF THE INVENTION

The present invention contemplates a system comprising one or more inflatable bladders which automatically test the stretch characteristics of stretch fabric, such as support hose, and provide an output plot representing that stretch characteristic to permit online at site testing of production line manufactured stretch fabric.

Figure 1A:
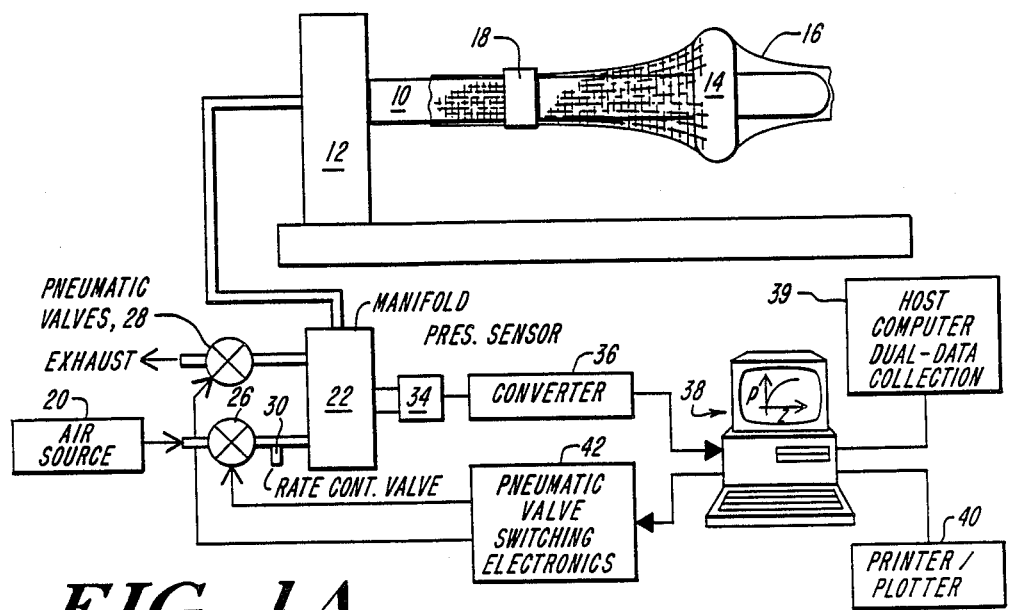
FIGS. 1A and 1B are schematic diagrams of the components of the apparatus of the present invention in embodiments for single and multiple site testing.
Figure 1B:
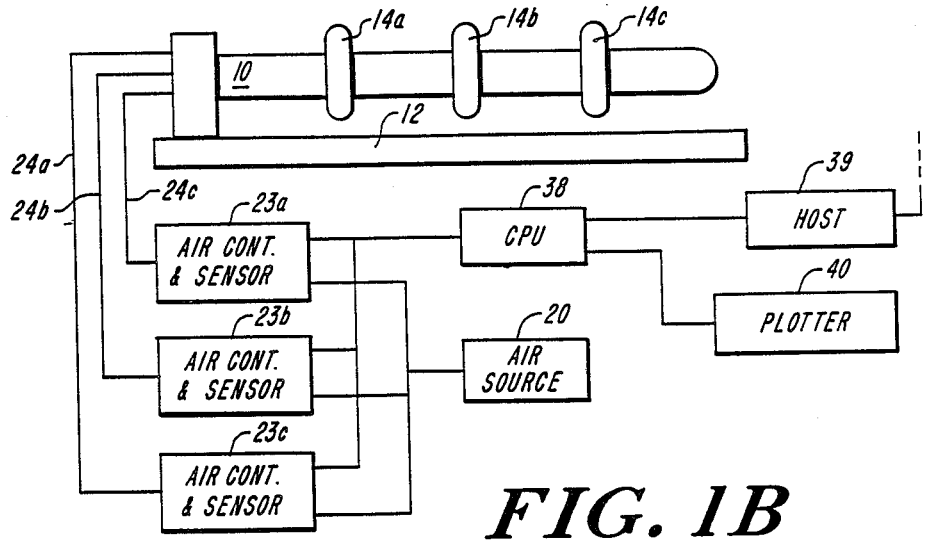
Figure 2:
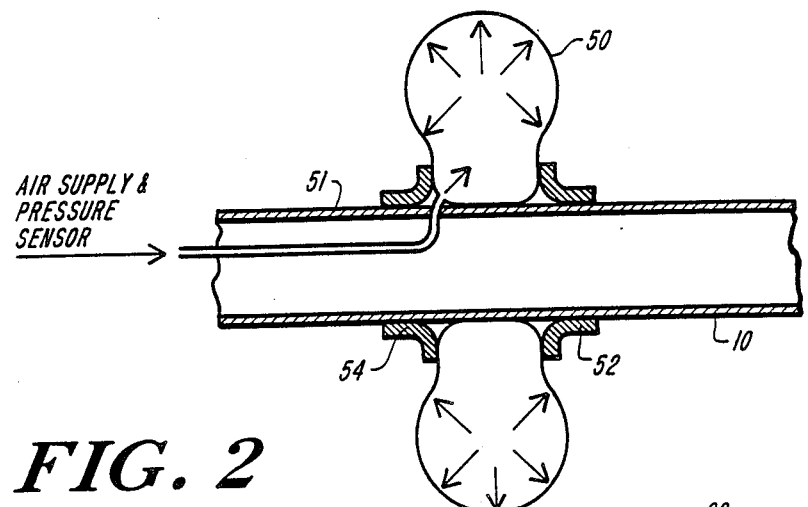
FIG. 2 illustrates one embodiment for the inflatable bladder of the apparatus of the present invention.

Referring now to an exemplary embodiment in FIGS. 1A, 1B and 2, a support tube 10 is shown supported horizontally by a base 12. Encircling support tube 10 is an annular, inflatable bladder 14, typically manufactured from an elastomeric material. Bladder 14 strength and resilience should be adapted to the characteristics of the material being tested. Placed over bladder 14 and support tube 10 is a stretchable fabric sample 16 such as support hose. Sample 16 is secured on support tube 10 by restraining collar 18 which may be an elastic band or other restraining means.

An air source 20, is connected to supply air through pneumatic on/off valve 26, rate control valve 30, manifold 22, and pipe 24 to the interior of support tube 10 and thence to bladder 14. A pneumatically controlled exhaust valve 28 connected to manifold 22 permits controlled deflation of the bladder 14. Rate control valve 30 controls the rate of air flow through manifold 22 and pipe 24 so that the volume air supplied as a function of time is the same from test to test allowing a meaningful comparison of pressure as a function of time from test to test. A pressure sensor 34 is connected to, and measures the air pressure inside, manifold 22 and thus inside bladder 14. Converter 36 converts the analog signal from pressure sensor 34 into binary machine readable electronic data.

A computer 38 receives, stores and processes data from the converter 36. A printer/plotter 40 is driven by computer 38 to provide a graphical display of the data. For example, air pressure can be plotted against time for several samples. Thereafter, a comparison of the stretch characteristics of the samples is possible. Pneumatic valve switching electronics 42 is connected to computer 38 and control pneumatic control valves 26, 28 to control inflation and deflation of the valves as described below. A host computer 39 may be provided to communicate with plural systems of the type shown in FIG. 1A (or FIG. 1B) for centralized data control.

With reference now to FIG. 1B there is shown an embodiment of the invention in which stretch characteristics testing can be made simultaneously at several points along a single stretch fabric or hose. Essentially FIG. 1B shows the use of three inflatable bladders 14A, 14B and 14C on a single support tube 10. Each bladder 14A, 14B and 14C is independently pressurized through respective air control and sense systems 23A, 23B and 23C each of which includes respective pneumatic valves 26 and 28, rate control valves 30, manifold 22, pressure sensors 34, converters 36 and pneumatic valve switching electronics 42. In this manner a separate pressure signal is supplied to the computer from the air control and sense systems 23A-23C for each of the bladders 14A-14C respectively.

Figure 3:
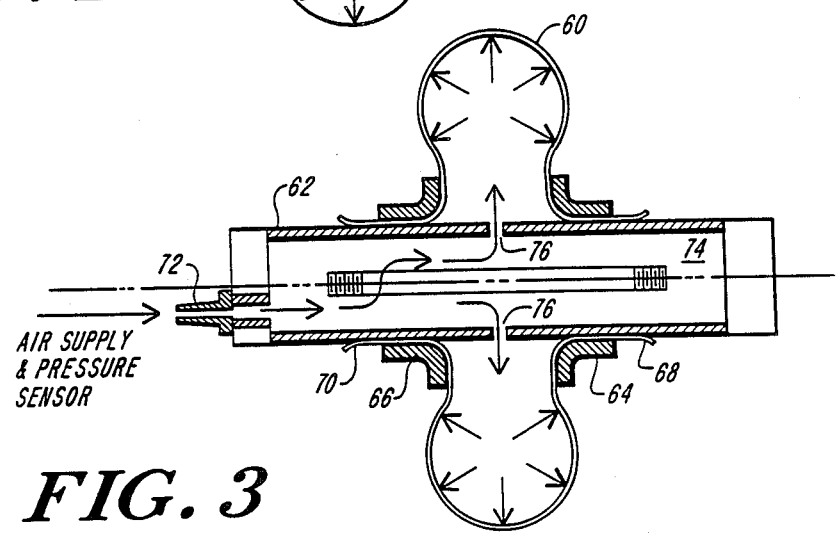
FIG. 3 illustrates an alternative embodiment for the inflatable bladder of the present invention.

Referring now to FIG. 2, a cross-section of one embodiment of the inflatable bladder 14 of the present invention is illustrated. In this embodiment, inflatable bladder 50 is similar to a small inner tube. Air is forced from air supply 20 via pipe 51, which is threaded through an aperture (not shown) in support tube 10, into inflatable bladder 50 via its inflation nipple. Rigid restraining rings 52, 54 are mounted peripherally upon support tube 10 to maintain inflatable bladder 50 in position on support tube 10.

Where plural bladders are placed on a single support tube, the bladder construction of FIGS. 2 and 3 is repeated for each bladder.

Referring now to FIG. 3, an alternative embodiment of the inflatable bladder of the present invention is illustrated. In this embodiment, inflatable bladder 60 comprises a band of elastomeric material through which is inserted support tube 62. Split rings 64, 66 are mounted on support tube 62, trapping perimeters 68, 70 respectively of inflatable bladder 60 between rings 64, 66 and support tube 10. Bolts are utilized to tighten rings 64, 66 holding inflatable bladder 60 securely in place during inflation. In this embodiment, air is directed from air supply 20 through port 72 into a chamber 74 within support tube 62. Air is admitted into inflatable bladder 60 from chamber 74 through one or more apertures 76 in support tube 62.

Figure 4C:
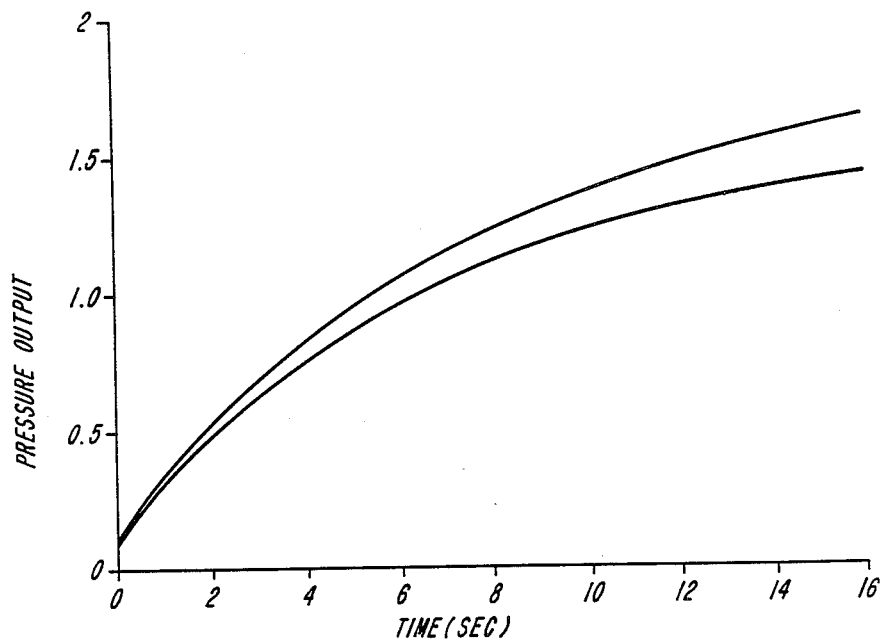
FIGS. 4A, 4B, 4C, 4D illustrate a typical graphic output generated by the apparatus of the present invention.
Figure 4:
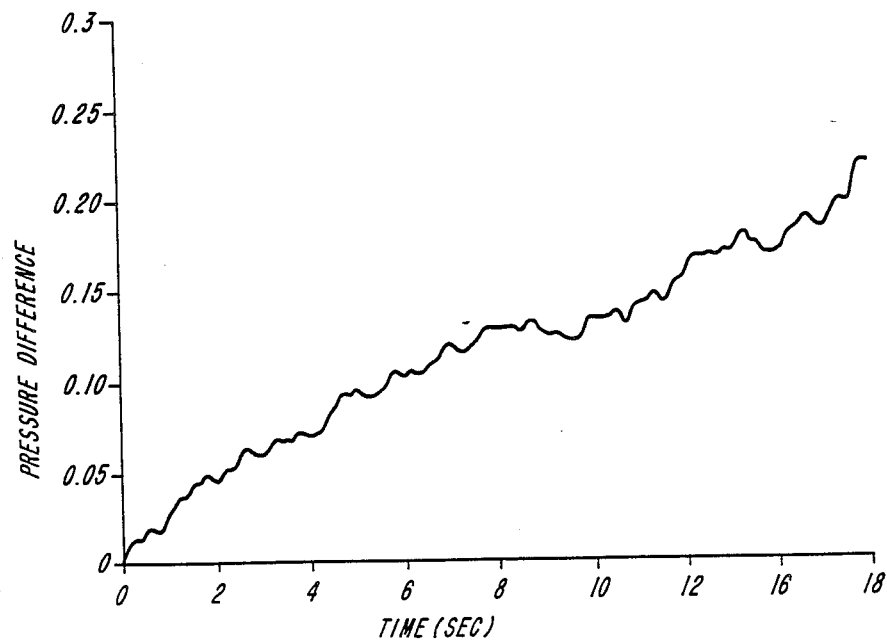
Figure 4A:
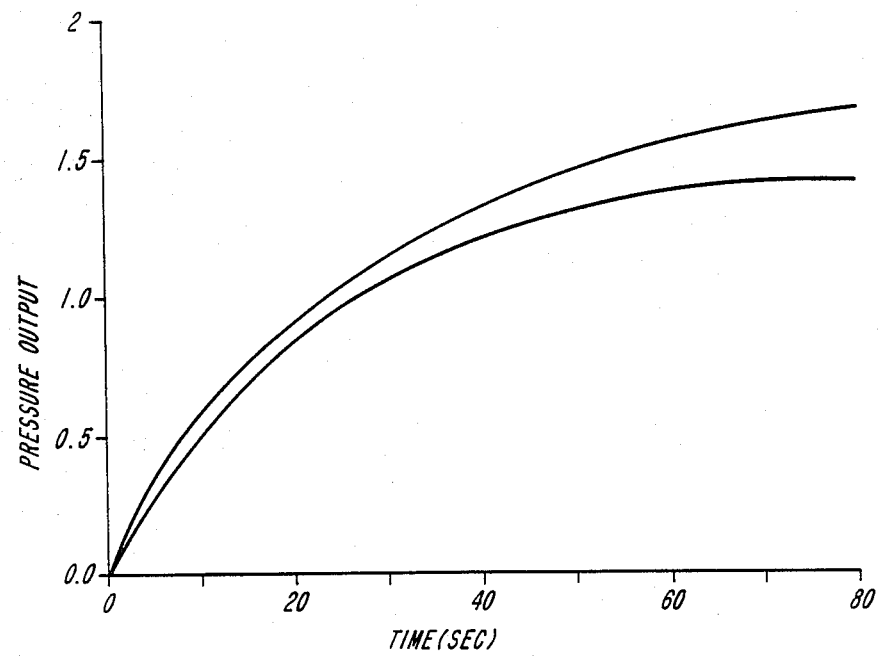
Figure 4B:
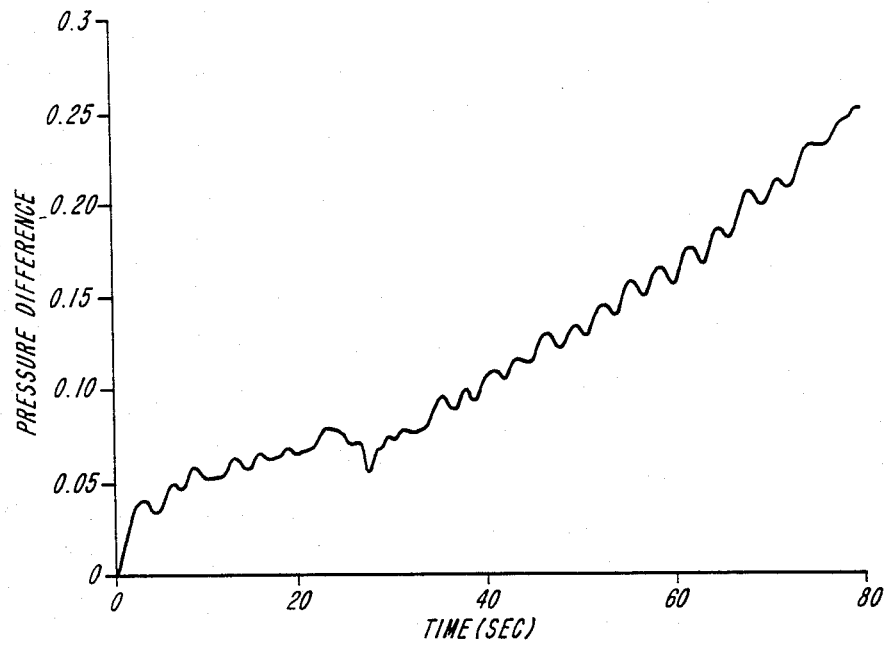

Referring now to FIGS. 4A, 4B, 4C and 4D examples of graphical output generated by the present invention are illustrated. In this example, bladder air pressure has been plotted against time in FIGS. 4A and 4C. The lower graph line indicates the pressure as a function of time required to inflate the bladder with no sample mounted. The upper graph line indicates the higher pressure required for inflation when a sample is mounted. Thus, the vertical distance between the lines reflects the stretch characteristics of the sample and is plotted in FIGS. 4B and 4D showing significantly different stretch characteristics.

Figure 5:
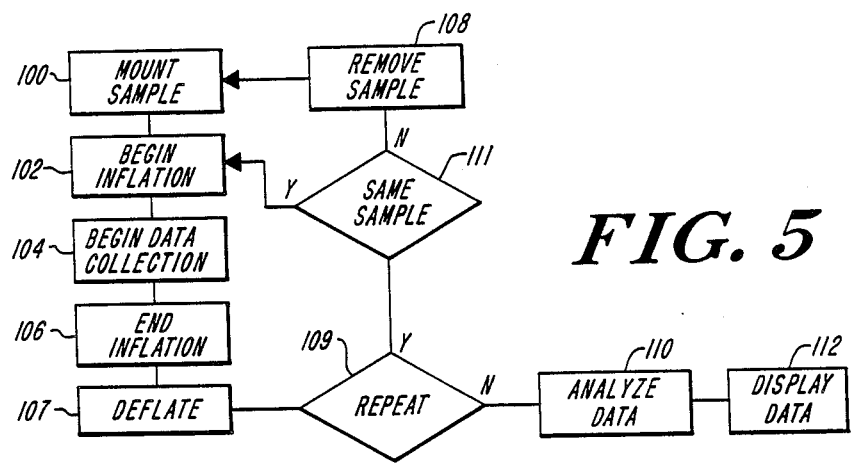
FIG. 5 is a flow chart of the fabric test cycle of the present invention.

Referring now also to FIG. 5, a flow chart of the testing process according to programmed control of computer 38 is illustrated. In step 100, the fabric sample is mounted on support tube 10 and secured by restraining collar 18. A constant rate flow of air from air supply 20 to inflatable bladder 14 is commenced in step 102 by opening valve 26 with valve 28 closed. During inflation, air pressure sensed by sensor 34 is collected by computer 38, via converter 36 in step 104. When the desired inflation has been achieved, which can be limited by time or pressure, the supply of air is terminated in step 106 by closing valve 26. The inflatable bladder is deflated in step 107 by opening valve 28. If repeated testing of the same sample is required, steps 100-107 are repeated by executing a decision step 100 to decision step 111. If a new sample is to be tested, decision step 111 leads to a step 108 where the old sample is removed and steps 100-107 are repeated. Otherwise, decision 111 branches to repeat a pre-selected number of cycles of steps 102-107 on the same sample. When sufficient data has been collected, it is analyzed, step 110, and displayed, for example, on a printer/plotter in step 112.

The operator of the present invention is thereby able to ascertain, by repeated testing of the same sample, the stretch degradation and stretch life of the sample. In addition, when more than one sample is tested, a comparison of respective stretch characteristics is facilitated. Storage and display of data also permits the operator to compare samples tested against a control sample quickly and accurately. A host computer 39 permits such comparisons from data collected by a plurality of computers 38 located in divers locations in the factory.

It will be appreciated that by adjusting rate control valve 30, the operator of the present invention can adapt the test for the variances of stretchability between different fabrics.

Described above are preferred embodiments of the present invention. Other modifications and alterations can be practiced within the spirit of the invention which it is accordingly intended to define only as indicated in the following claims.

What is claimed is:

1. A stretch fabric measuring station comprising:
   a support member adapted to receive a section of stretch fabric to be tested;
   at least one inflatable bladder securely mounted peripherally on said support member; and
   means for inflating said inflatable bladder, and
   means for determining the stretch characteristics of the fabric to be tested from the air pressure within said inflatable bladder.

2. The apparatus of claim 1 further including means for releasably securing a stretch fabric to said support member.

3. The apparatus of claim 1 wherein:
   said inflatable bladder comprises an elastomeric toroid having an aperture for the ingress and egress of air; and
   said inflating means comprises air supply means connected to said inflatable bladder.

4. The apparatus of claim 1 wherein:
   said inflatable bladder comprises a band of elastomeric material;
   said support member includes a conduit for the passage of air therethrough and at least one aperture for the passage of air between said support member and said inflatable bladder; and said inflating means comprises air supply means connected to said inflatable bladder.

5. The apparatus of claims 3 or 4 further comprising restraining means releasably securing said inflatable bladder in mounted position on said support member.

6. The apparatus of claim 4 wherein said restraining means comprises:
   at least two split rings peripherally mounted on said support member with opposing edge portions of said band therebetween; and
   at least one clamp restraining each said at least one split ring against axial movement on said support member thereby securing the bladder edge portions to said support member.

7. The apparatus of claim 1 wherein said inflating means further comprises:
   means for defining a rate of airflow between an air supply means and said inflatable bladder; and
   a sensor connected to said defining means to provide an indication of air pressure inside said bladder.

8. The apparatus of claim 7 further comprising:
   electronic data processing means;
   means connected to said sensor and said electronic data processing means for converting air pressure data of said sensor into machine readable format; and
   means connected to said data processing means for displaying said air pressure data as a function of time.

9. The apparatus of claim 8 further comprising means associated with said electronic data processing means for controlling said rate defining means.

10. The apparatus of claim 1 further including data processing means operative to cause said bladder to inflate at a defined rate and deflate through one or more cycles.

11. The apparatus of claims 8 or 10 wherein:
    plural bladders are mounted to said support member; and
    means are provided to simultaneously inflate said plural bladders and said sensor is adapted to sense pressure in each bladder independently.

12. A method for measuring the stretch characteristic of fabrics, comprising:
    positioning a fabric sample over at least one inflatable bladder mounted on a support member;
    releasably securing said fabric sample to said support member;
    inflating said inflatable bladder; and
    determining the pressure of the air within said inflatable bladder as a function of air supplied to said at least one bladder.

* * * * *

UNITED STATES PATENT AND TRADEMARK OFFICE
CERTIFICATE OF CORRECTION

PATENT NO. : 4,866,991
DATED : September 19, 1989
INVENTOR(S) : Ming K. Tse It is certified that error appears in the above-identified patent and that said Letters Patent is hereby corrected as shown below:

ON TITLE PAGE:

In line [76] Inventor:, "FLINT LOCK Rd." should read
--Flintlock Rd.--.

In Column 2, line 28, "FIG. 3 . illustrates" should read
--FIG. 3 illustrates--.

In Column 4, line 48, "member; and" should read --member;--.

Signed and Sealed this

Second Day of June, 1992

*Attest:*

DOUGLAS B. COMER

*Attesting Officer*    *Acting Commissioner of Patents and Trademarks*